US010783996B2

(12) United States Patent
Westermann et al.

(10) Patent No.: US 10,783,996 B2
(45) Date of Patent: Sep. 22, 2020

(54) METHOD AND SYSTEM FOR ESTABLISHING NETWORK CONNECTION TO A HEARING AID

(71) Applicant: Widex A/S, Lynge (DK)

(72) Inventors: Soren Erik Westermann, Espergaerde (DK); Svend Vitting Andersen, Espergaerde (DK); Anders Westergaard, Herlev (DK); Niels Erik Boelskift Maretti, Birkerod (DK)

(73) Assignee: Widex A/S, Lynge (DK)

( * ) Notice: Subject to any disclaimer, the term of this patent is extended or adjusted under 35 U.S.C. 154(b) by 254 days.

(21) Appl. No.: 15/600,173

(22) Filed: May 19, 2017

(65) Prior Publication Data

US 2017/0257713 A1    Sep. 7, 2017

Related U.S. Application Data

(63) Continuation of application No. PCT/EP2015/077205, filed on Nov. 20, 2015.

(51) Int. Cl.
*G16H 40/67* (2018.01)
*G16H 40/40* (2018.01)
(Continued)

(52) U.S. Cl.
CPC ............ *G16H 40/67* (2018.01); *G16H 10/60* (2018.01); *G16H 10/65* (2018.01); *G16H 40/40* (2018.01);
(Continued)

(58) Field of Classification Search
CPC .. H04R 25/505; H04R 25/554; H04R 25/558; H04R 2225/39; H04R 2225/55;
(Continued)

(56) References Cited

U.S. PATENT DOCUMENTS 7,257,372 B2   8/2007  Kaltenbach et al.
8,166,312 B2   4/2012  Waldmann
(Continued)

FOREIGN PATENT DOCUMENTS

EP    1 252 799 A2   10/2002
EP    0 567 535 B1    8/2003
(Continued)

OTHER PUBLICATIONS

International Search Report of PCT/EP2015/077205, dated Feb. 5, 2016. [PCT/ISA/210].

*Primary Examiner* — Sunita Joshi
(74) *Attorney, Agent, or Firm* — Sughrue Mion, PLLC

(57) ABSTRACT

A system, method, hearing aid and software for providing a network connection for a computer device to at least one hearing aid having a gateway to the Internet. The system includes a user account server providing a user account database, each user account includes a unique identity for an associated hearing aid; a control server providing a hearing aid connection register including the unique identity of hearing aids associated with current connection information; and a network connection handling element for detecting the presence of a wireless connection between the hearing a and gateway, and for uploading current connection information to the control server. On receiving connection information, the control server updates the hearing aid connection register, and provides the current connection information to a requesting computer device. The computer device can establish a direct connection to the hearing aid based on current connection information requested from the control server.

20 Claims, 5 Drawing Sheets

(51) Int. Cl.
*H04R 25/00* (2006.01)
*G16H 10/60* (2018.01)
*G16H 50/30* (2018.01)
*H04W 12/06* (2009.01)
*H04W 48/18* (2009.01)
*G16H 10/65* (2018.01)
*H04W 76/14* (2018.01)
*H04W 4/80* (2018.01)

(52) U.S. Cl.
CPC ........... *G16H 50/30* (2018.01); *H04R 25/505* (2013.01); *H04R 25/554* (2013.01); *H04R 25/558* (2013.01); *H04R 25/70* (2013.01); *H04W 4/80* (2018.02); *H04W 12/06* (2013.01); *H04W 48/18* (2013.01); *H04W 76/14* (2018.02); *H04R 2225/39* (2013.01); *H04R 2225/55* (2013.01); *H04R 2225/67* (2013.01)

(58) Field of Classification Search
CPC .... H04R 2225/67; G16H 40/67; G06F 21/35; H04W 4/02; H04W 8/005
See application file for complete search history.

(56) References Cited

U.S. PATENT DOCUMENTS

| | | | |
|---|---|---|---|
| 9,219,966 B2* | 12/2015 | Wang | H04W 8/005 |
| 2003/0138109 A1* | 7/2003 | Bindner | H04R 25/70 |
| | | | 381/60 |
| 2005/0283263 A1* | 12/2005 | Eaton | H04R 25/70 |
| | | | 700/94 |
| 2008/0107278 A1 | 5/2008 | Roeck et al. | |
| 2011/0176686 A1 | 7/2011 | Zaccaria | |
| 2011/0257994 A1 | 10/2011 | Givens et al. | |
| 2012/0183164 A1 | 7/2012 | Foo et al. | |
| 2013/0272554 A1* | 10/2013 | Sommer | H04M 1/05 |
| | | | 381/314 |
| 2016/0212552 A1* | 7/2016 | Schneider | H04L 67/06 |

FOREIGN PATENT DOCUMENTS

| | | |
|---|---|---|
| EP | 1 083 769 B1 | 6/2010 |
| EP | 2 206 362 B1 | 1/2014 |
| EP | 2 760 225 A1 | 7/2014 |
| EP | 2 799 985 A2 | 11/2014 |
| WO | 2011/128462 A2 | 10/2011 |
| WO | 2014/094859 A1 | 6/2014 |
| WO | 2014/094866 A1 | 6/2014 |

* cited by examiner

METHOD AND SYSTEM FOR ESTABLISHING NETWORK CONNECTION TO A HEARING AID

BACKGROUND OF THE INVENTION

The present invention relates to hearing aids. The invention, more particularly, relates to a method for establishing network connection to a hearing aid over the Internet. Also, the invention relates to a system for establishing a network connection.

Hearing aid manufacturing companies design, develop and manufacture hearing instruments for distribution by independent, credentialed, licensed hearing health care professionals providing service and support for hearing impaired customers in compliance with all applicable state, federal and professional regulations and law.

The hearing health care professionals are an instrumental part of the processed selection and delivery of the hearing aids to the hearing impaired customer because they, with their technical understanding of the hearing aid, and their knowledge of hearing aids and rehabilitation and supported by professional fitting tools provided by the hearing aid manufacturing company can provide beneficial individualized fitting solutions tailored to satisfy the needs of the individual customer.

The sales channels bringing the hearing aids from the manufacturing companies to the hearing impaired customer are undergoing significant structural changes these years. We still see many specialty stores staffed with hearing health care professionals selling and fitting hearing aids. A major challenge is that the hearing aid user has to visit a hearing health care professional several times in order to reach a solution alleviating his hearing loss. Various attempts to provide remote fitting over the Internet have been done.

The Internet has grown to be very heterogeneous, and the lack of Internet addresses in the IPv4 Internet protocol has led to the dynamic IP allocation when a first device is connected, and where the same address may be used by a second device once the first device has been disconnected. Another issue is that the device is often a part of a local area network behind a firewall.

SUMMARY OF THE INVENTION

The purpose of the invention is to provide a method for establishing a network connection to at least one hearing aid via the Internet, whereby e.g. a hearing health care professional may retrieve data from a hearing aid and adjust settings of the hearing aid.

This purpose is according to the invention achieved by a method for providing a network connection to at least one hearing aid via the Internet, wherein the at least one hearing aid is connected to the Internet via a gateway. The method comprises the steps of providing a plurality of user accounts in a user account server accessible over the Internet, each user account including a unique identity of associated hearing aids; detecting the presence of a wireless connection between the at least one hearing aid and the gateway; communicating the current connection information to a control server; providing, in the control server, a hearing aid connection register containing the unique identity of hearing aids and corresponding communicated current connection information; requesting, from a computer device, the control server to provide the current connection information for the at least one hearing aid by providing the associated unique identity; and establishing, from the computer device, a direct connection to the at least one hearing aid based on the current connection information retrieved from the control server.

In one embodiment an Internet enabled personal communication device and the at least one hearing aid are connected for establishing a wireless connection, whereby the personal communication device becomes a gateway for the at least one hearing aid to a user account server over the Internet. In one embodiment, the network connection handling element is contained in the hearing aid and is adapted for detecting the connection to the Internet. In another embodiment, the network connection handling element is contained in the personal communication device and is adapted for detecting the presence of the short range wireless connection to the at least one hearing aid.

When the computer device is connected to the hearing aid via the gateway, the hearing health care professional may program the at least one hearing aid for alleviating the hearing loss. The programming may take place during a call, e.g. a video call as provided by Skype®, between the hearing health care professional and the hearing aid user.

The user account server and the control server have two different responsibilities and the two servers are preferably two separate entities. Preferably, the user account server automatically updates the hearing aid connection register of the control server upon creation of new user accounts. As personal communication devices may access the Internet via several routes—e.g. WLAN and cellular—and consequently have separate IP addresses for the different routes, the hearing aid connection register of the control server is in various embodiments prepared for handling multiple connection information elements.

In an embodiment, a hearing healthcare professional is programming the at least one hearing aid during a fitting session by means of a computer program running on the computer device, wherein the computer program retrieves an unique identity for the at least one hearing aid from the user account server retrieves the associated IP address from the hearing aid connection register administered by the control server.

According to a second aspect of the invention there is provided a system for providing a network connection for a computer device to at least one hearing aid having a gateway to the Internet. The system comprises a user account server accessible over the Internet, and providing a user account database, each user account including an unique identity for an associated hearing aid; a control server providing a hearing aid connection register including the unique identity of the hearing aids associated with the current connection information; and a network connection handling element adapted for detecting the presence of a wireless connection between the at least one hearing aid and the gateway, and for uploading current connection information to the control server. The control server is adapted for updating the connection information in the hearing aid connection register when receiving communicated connection information, and for providing the current connection information to a computer device upon request. The computer device is adapted for establishing a direct connection to the at least one hearing aid based on the current connection information requested from the control server.

According to a third aspect of the invention there is provided a computer-readable storage medium having computer-executable instructions, which when executed on a computer device are adapted for programming at least one hearing aid during a fitting session under control by a hearing healthcare professional. The computer-executable instructions are adapted for launching a fitting session application on the computer device; accessing from the fitting session application a user account server over the Internet for retrieving a user account for the user of the at least one hearing aid to be programmed, the user account containing a unique identity of the at least one hearing aid; retrieving connection information for the at least one hearing aid from the hearing aid connection register administered by a control server; and establishing a direct connection for programming at least one hearing aid based on the connection information retrieved from the control server.

According to a fourth aspect of the invention there is provided a hearing aid having a unique identity and being adapted to be connected to a computer device via the Internet. The hearing aid comprises a network connection handling element being adapted to detect the presence of a wireless connection between the hearing aid and a gateway to the Internet, and to communicating current connection information for the hearing aid to a control server. Hereby the computer device may request the current connection information for the hearing aid from said control server based on the unique identity, and establish a direct connection to the hearing aid.

BRIEF DESCRIPTION OF THE DRAWINGS

The invention will be described in further detail with reference to preferred aspects and the accompanying drawing, in which.

DETAILED DESCRIPTION

Figure 1:
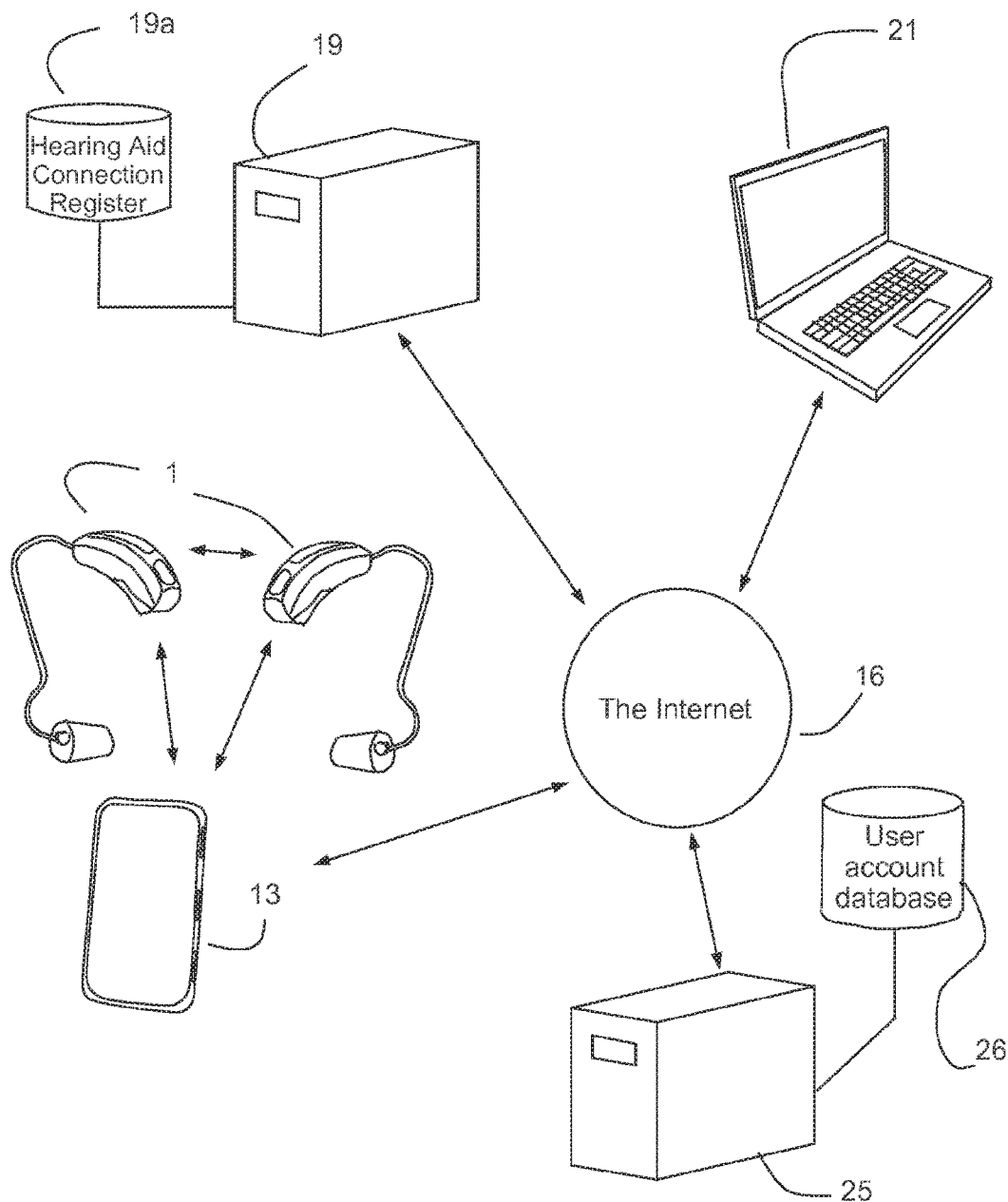
FIG. 1 illustrates schematically a system for providing a network connection to at least one hearing aid according to a first embodiment of the invention.

Reference is made to FIG. 1, which schematically illustrates a system for providing a network connection for a computer device 21 to at least one hearing aid 1 having a gateway the Internet 16, according to a first embodiment of the invention. Prior to use, the settings of the hearing aid are set and adjusted by a hearing care professional according to a prescription. The prescription is provided by an audiologist and is based on a hearing test, resulting in a so-called audiogram, of the performance of the hearing-impaired user's unaided hearing. The prescription is developed to reach a setting where the hearing aid will alleviate a hearing loss by amplifying sound at frequencies in those parts of the audible frequency range where the user suffers a hearing deficit.

Hearing aids are often provided to a hearing impaired user as a set of binaural hearing aids 1. The set of hearing aids 1 have preferably an inter-ear communication channel based on a suitable communication protocol, such as the Bluetooth™ Low Energy protocol. The set of hearing aids 1 communicates preferably with the personal communication device 13—here shown as a smartphone. The two hearing aids 1 are illustrated as Behind-The-Ear hearing aids having customized ear plugs. However the invention is applicable for any type of hearing aid 1 being able to communicate with the personal communication device 13 via a wireless connection.

The personal communication device 13 according to the invention is Internet enabled which means that the personal communication device 13 may access the Internet 16 via a wireless Internet connection (e.g. WLAN such as $802.11_{a, b\ or\ g}$), or a cellular data connection (e.g. WCDMA or LTE). Advantageously, the personal communication device 13 has the ability to download and launch application software from an app store via the Internet. The term "app" is short for application software, which is a set of one or more programs designed to carry out operations for a specific application. Application software cannot run on itself but is dependent on system software to execute.

A user account server 25 is accessible over the Internet and is providing a user account database 26; each user account including a unique identity or identifier for an associated hearing aid 1. Furthermore, a control server 19 is providing a hearing aid connection register 19a holding unique identities for hearing aids with associated connection information. The personal communication device 13, or the hearing aids 1, includes a network connection handling element 43 being adapted for detecting the presence of the short range wireless connection between the at least one hearing aid 1 and said gateway. The network connection handling element 43 is adapted for uploading current connection information to the control server 19. In the embodiment shown in FIG. 2, the network connection handling element 43 is integrated as a part of the hearing aid 1, while the embodiment shown in FIG. 4 has the network connection handling element 43 integrated as a part of the personal communication device 13. The control server 19 is adapted for updating the connection information in the hearing aid connection register 19a when receiving uploaded connection information. The control server 19 furthermore provides the connection information to a computer device 21 upon request. The computer device 21 is adapted for establishing a direct connection to the at least one hearing aid 1 based on the connection information requested from the control server 19.

The connection information includes the current IP address of the hearing aid 1. Furthermore, the connection information may also include the port number of the hearing aid 1, as an IP address is always associated with a port of the host. The port is the endpoint of communication in the host's operating system. In some situations it may be advantageous to identify in the connection information the protocol type of the communication.

Figure 5:
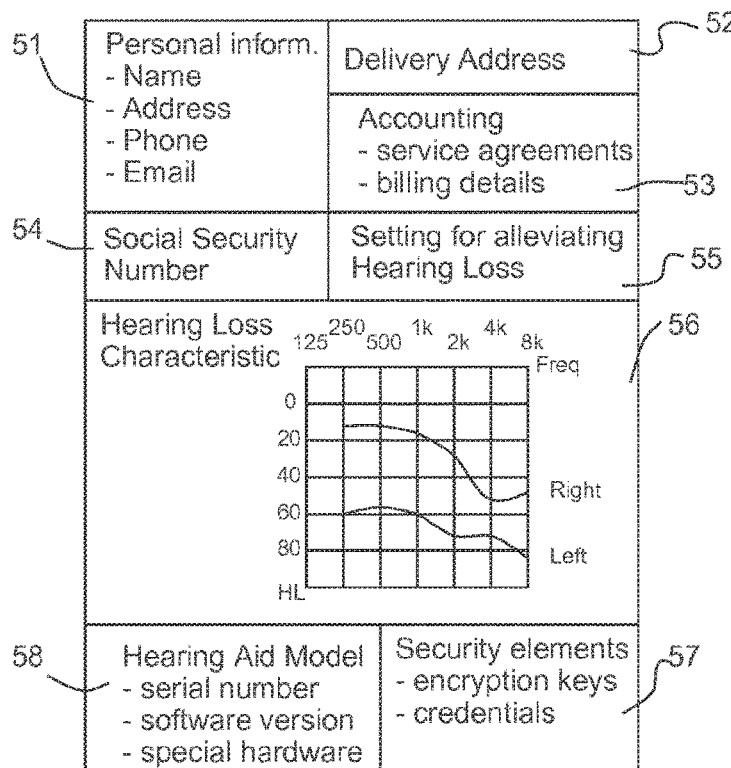
FIG. 5 illustrates schematically the data structure of a user account handled in the network connection system according to an embodiment of the invention.

The data structure of the data in the user account database 26 maintained by the user account server 25 is schematically illustrated in FIG. 5. The data fields of the user account are for some data fields synchronized with data stored in the hearing aid 1. The data set in a user account includes a personal information data field 51, which typically is the first data field filled out by the user when creating an account. The personal information includes name, address and additional contact data like phone number and e-mail address. A delivery address data field 52 defines the delivery address for physical products to be delivered to the hearing aid user. The delivery address is specified by the owner of the account and may be identical to the home address identified in the personal information data field 51, or another delivery address, e.g. a preferred supermarket or retail store in case the account is linked to a membership in a warehouse club.

In an accounting data field 53, a service provider or any authorized hearing aid professional may enter respective service agreements and the user may enter invoicing details, such as that an invoice is preferred or that debiting of a specified credit card is preferred. The service agreements may refer to a specified fitting session, a hearing test, purchase of a specified set of hearing aids, subscription to a specified set of hearing aids, and upgrade of an existing set of hearing aids, batteries, or replacement parts. The user has the right to approve the service agreements and enter invoicing details, while the service providers may enter service agreement details as price and conditions supported by one or more documents and use entered invoicing details for their own accounting. The accounting data field 53 will only contain one service agreement, and if several service agreements are initiated, supplementing accounting data fields 53 will be created. Only parties to a service agreement are granted Data Retrieval Rights to these data fields 53.

In a social security data field 54, the user may enter his birthday information and social security number, which may be used by the social authorities in cases these are committed to pay a part of the sales prize or subscription fees.

When the authorized hearing healthcare professional or audiologist tests the hearing of a client, he obtains the results in an audiogram, which is a graph showing the hearing loss measured in decibels for standardized frequencies in Hertz. The threshold of hearing is plotted relative to a standardized curve that represents "normal" hearing, in dB (HL). The authorized hearing aid professional may store the hearing loss characterization in a dedicated Hearing Loss Characterization data field 56, whereby the authorized hearing aid professional or another authorized hearing aid professional at a later point of time may assess changes in the hearing capability of the client.

When the authorized hearing aid professional has determined the hearing loss of his client and an appropriate hearing aid has been chosen, the authorized hearing aid professional sets the hearing aid compensation profile parameters (fitting) in an interactive dialogue with the client. Once the fitting has been completed, the settings are stored in the hearing aid and afterward synchronized with a data field 55 in the user account containing the settings for alleviating Hearing Loss.

For each user account there is provided a data field 57 containing security elements as credentials for accessing one or more data fields in the hearing aid user account and secure keys for establishing a secure connection between the computer device 21 and the at least one hearing aid 1. The hearing aid user may by means of the stored security elements edit credentials via a web-interface. The user account manager may by means of certificates control persons allowed to Read and Edit data in the user account and thereby in the hearing aid 1, and the hearing user may delegate these rights to third parties.

Finally the hearing aid account includes a data field 58 identifying each of the hearing aids 1 associated with the account, the hearing aids 1 being identified by manufacturer, hearing aid model, serial number, and software version. The unique identity for the hearing aid 1 is stored as an element in the data field 58.

Figure 2:
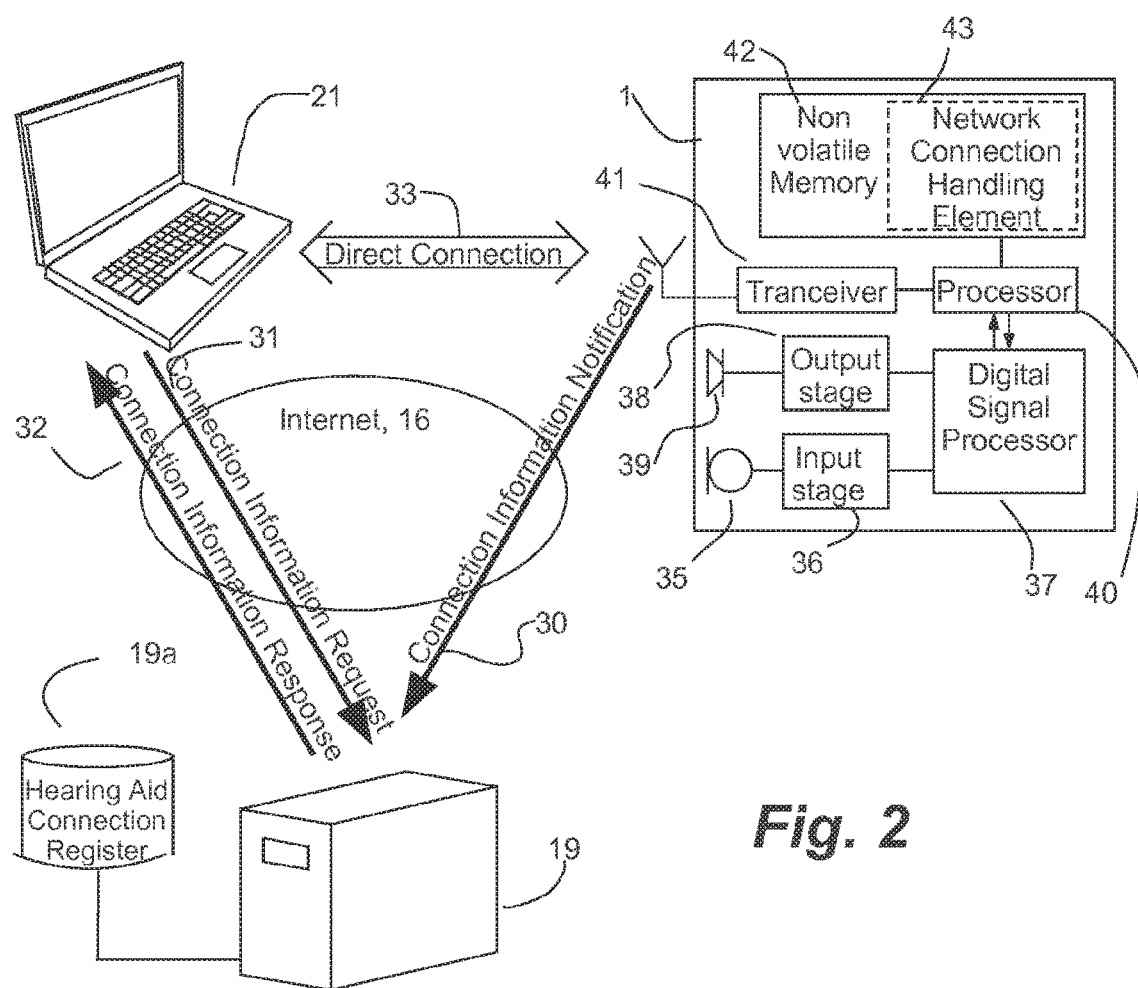
FIG. 2 illustrates schematically a system for providing a network connection to at least one hearing aid according to a second embodiment of the invention.

Referring to FIG. 2, it is seen that the hearing aid 1 comprises an input transducer 35 or microphone for picking up the acoustic sound and converting it into electric signals. The electric signals from the input transducer 35 are amplified and converted into a digital signal in an input stage 36. The digital signal is fed to a Digital Signal Processor 37 (DSP) being a specialized microprocessor with its architecture optimized for the operational needs of the digital signal processing task, i.e. for carrying out the amplification and conditioning according to a predetermined setting in order to alleviate a hearing loss by amplifying sound at frequencies in those parts of the audible frequency range where the user suffers a hearing deficit. The output from the Digital Signal Processor 37 is fed to an output stage 38 for reproduction by an output transducer 39 or speaker. The output stage 38 may apply Delta-Sigma-conversion to the digital signal for forming a one-bit digital data stream fed directly to the output transducer 39, the output stage thereby operating as a class D amplifier.

The hearing aid 1 has a processor 40 being a processing and control unit carrying out instructions of a computer program by performing the logical, basic arithmetric, control and input/output (I/O) operations specified by the instruction in the programs. The processor 40 includes an inherent volatile memory requiring power to maintain the stored information. The processor 40 is further connected to a non-volatile memory 42 which retains stored information even when not powered. Furthermore, the hearing aid 1 has a transceiver 41 for establishing a wireless connection to a gateway to the Internet 16. This gateway may be the personal communication device 13, a router (e.g. WLAN) in private domain, or a hotspot in a public domain. A hotspot is a physical location that offers Internet access over a wireless local area network (WLAN) through the use of a router connected to a link to an Internet service provider. Hotspots typically use Wi-Fi technology.

In this embodiment the hearing aid 1 comprises a network connection handling element 43 stored as a software program in the non-volatile memory 42. The network connection handling element 43 detects when a new network connection to the hearing 1 has been established—e.g. a connection to a hotspot or to a router at home, and when the current Internet address has been identified, the network connection handling element 43 transmits a connection information notification 30 over the Internet 16 to the control server 19. The address of the control server 19 may advantageously be preprogrammed into the network connection handling element 43. The connection information notification 30 links a unique identity for the hearing aid 1 to its current connection information. The transmission of the connection information notification 30 is trigged by an event, e.g. a connection being established via a gateway to the Internet. Hereby the control server 19 is able to maintain its hearing aid connection register 19a as a look-up table in which the unique identity for the hearing aid 1 may be translated to the current connection information for the network connection handling element 43 and thereby the hearing aid 1.

The Internet is adapted to relay datagrams across network boundaries based on the Internet Protocol (IP). The routing function according to the Internet protocol enables internetworking, and essentially establishes the Internet. The Internet Protocol has the task of delivering packets from the source host to the destination host solely based on the IP addresses in the packet headers. For this purpose, the Internet Protocol defines packet structures that encapsulate the data to be delivered. It also defines addressing methods that are used to label the datagram with both source and destination IP addresses. When sending the connection information notification 30, the current connection information of the network connection handling element 43 is present as source address of the data packet embodying the connection information notification 30, and the unique identity for the hearing aid 1 is contained in the data packet. The control server 19 extracts these two elements and updates a hearing aid connection register 19a accordingly.

The network connection handling element 43 serves several purposes—it monitors status of the hearing aid's connectivity, handles session security, and notifies the current connection information to the hearing aid connection register 19a. The network connection handling element 43 is embedded into the hearing aid before it leaves the factory, and some elements may be stored in the non-volatile memory 42 and some elements as security elements and certificates in a non-editable memory.

When a hearing care professional needs to adjust the setting of a specific hearing aid user's hearing aid 1, he may via the computer device 21 access the specific hearing aid user's user account from the user account server 25 from where he may retrieve the unique identity for the at least one hearing aid 1 in question. Preferably the fitting software running on the computer device 21 automatically sends a connection information request 31 from the account based on the unique identity for the at least one hearing aid 1 in question to the control server 19. Based upon a look-up in the hearing aid connection register 19a, the control server 19 responds to the connection information request 31 by sending a connection information response 32 containing the current Internet address of the at least one hearing aid 1 based on the unique identity stored in the user account.

Figure 3:
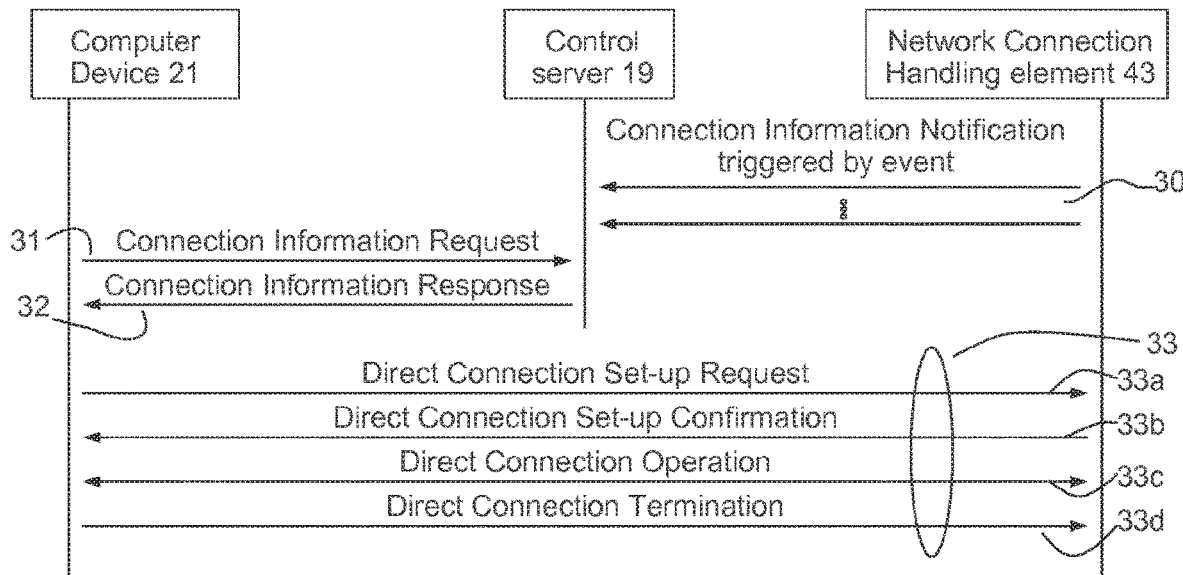
FIG. 3 illustrates schematically the data exchange in the network connection system according to an embodiment of the invention.

As shown in FIGS. 2 and 3, the computer device 21 then starts to set up a direct connection 33 preferably using UDP (User Datagram Protocol) hole punching (used for setting up connections between Internet hosts in private networks using network address translators) for establishing a bidirectional UDP connection. The computer device 21 sends a direct connection set-up request 33a to the network connection handling element 43, and if the hearing aid 1 is still on-line, the network connection handling element 43 confirms the request by sending a direct connection set-up confirmation 33b. Hereafter, the computer device 21 and the network connection handling element 43 start to exchange payloads in a bi-directional data packet exchange or direct connection operation 33c. The payload may include data for upload from the hearing aid 1, such as logging data and settings, and download of data to the hearing aid 1, such as adjusted settings for the hearing loss correction, instructions for enabling or disabling features in the hearing aid 1, and instructions for configuring the hearing aid 1. The computer device 21 disconnects the direct connection by sending a direct connection termination instruction 33d to the network connection handling element 43 once the data packets have been successfully exchanged.

Figure 4:
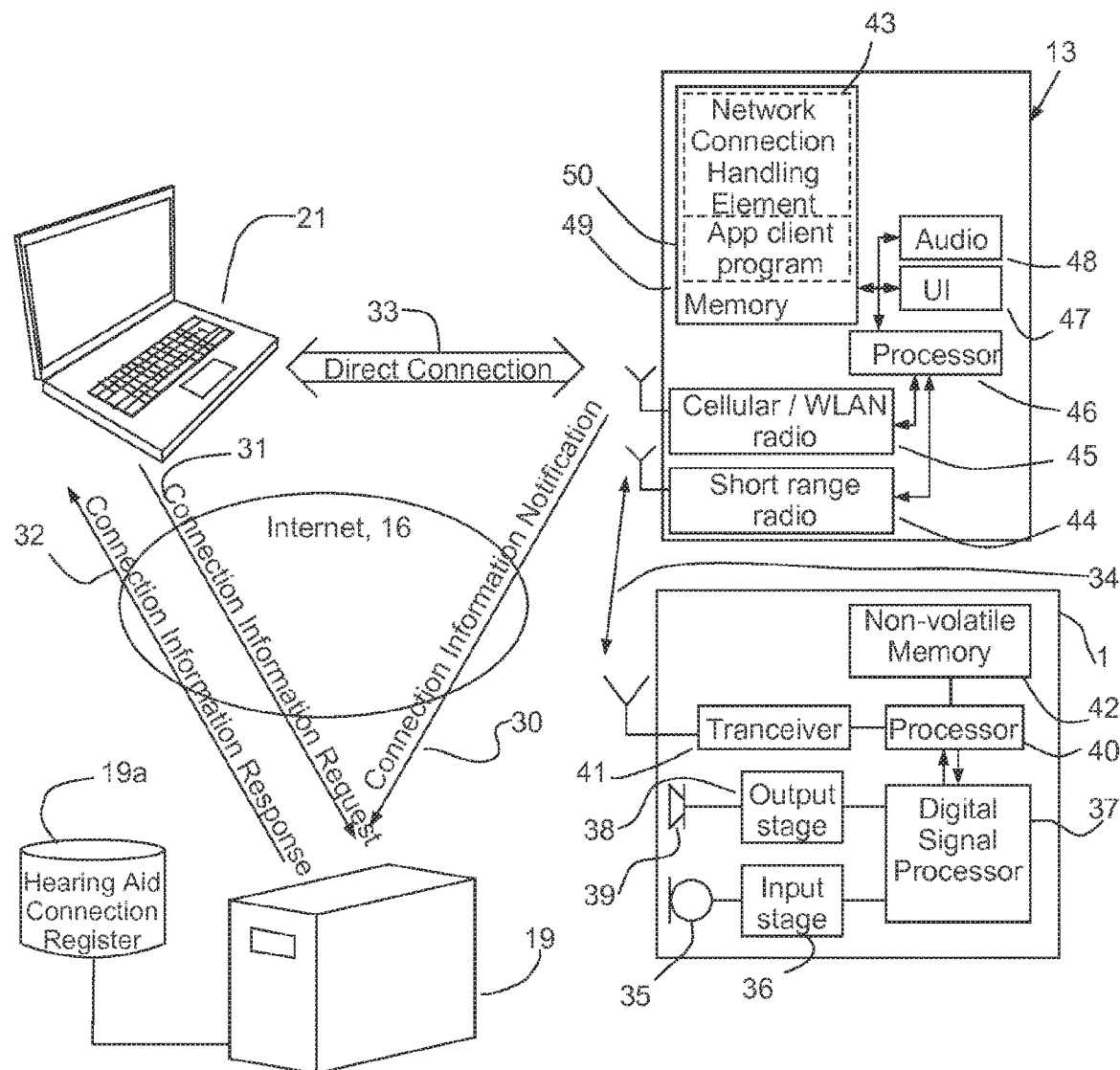
FIG. 4 illustrates in further details the embodiment of the invention shown in FIG. 1.

FIG. 4 illustrates in further details the embodiment of the invention shown in FIG. 1. The hearing aid 1 comprises the input transducer 35 for picking up the acoustic sound and converting it into electric signals being amplified and converted into a digital signal in the input stage 36. The digital signal is fed to the Digital Signal Processor 37 in which the amplification and conditioning is carried out according to the predetermined setting in order to alleviate a hearing loss by amplifying sound at frequencies in those parts of the audible frequency range where the user suffers a hearing deficit. The output from the Digital Signal Processor 37 is via the output stage 38 fed to the output transducer 39 for reproduction.

The processor 40 is connected to the non-volatile memory 42 and to the transceiver 41 for establishing a wireless connection to a gateway to the Internet 16. This gateway may be the personal communication device 13.

The personal communication device 13 is according the present embodiment a smartphone. The personal communication device 13 includes a processor 46 controlling the operation of audio elements 48 (like a speaker and a microphone) and user interface (UI) elements 47 (like a touch screen or keys and a display). Furthermore the processor 46 controls the operation of a long range radio 45 serving various mobile communication standards and WLAN standards connecting the personal communication device 13 to the Internet 16.

A short range radio 44 connects the personal communication device 13 to the hearing aid 1 by means of the Bluetooth Low Energy protocol. The personal communication device 13 has memory 49 (e.g. EEPROM)—in which a hearing aid control app 50 is stored. The personal communication device 13 is adapted to present the hearing aid control app 50 on a touch screen to the hearing aid user. The hearing aid control app 50 is adapted to offer control elements for the operation of the hearing aid.

In the embodiment shown in FIG. 4, the hearing aid control app 50 of the personal communication device 13 hosts the network connection handling element 43. The transceiver 41 may establish competing Internet connections, e.g. via the cellular network and via a public hotspot or a router at home. The network connection handling element 43 identifies the current connection information for the Internet connections identified. The network connection handling element 43 detects the presence of the short range communication channel between the personal communication device 13 and the hearing aid 1; and the long range communication channel from the personal communication device 13 to the Internet 16.

When the short range communication channel and long range communication channel both are present, the network connection handling element 43 transmits a connection information notification 30 as shown in FIG. 3 over the Internet 16 to the control server 19 whose IP address may be preprogrammed into the network connection handling element 43. The connection information notification 30 provides the unique identity for the hearing aid 1 linked to the current connection information.

The transmission of the connection information notification 30 is trigged by an event, i.e. both the short range communication channel and long range communication channel becoming present. Hereby the control server 19 is able to maintain its hearing aid connection register 19a as a look-up table in which the unique identity for the hearing aid 1 may be translated to the current connection information of the network connection handling element 43. The connection information in hearing aid connection register 19a for a unique identity for the hearing aid 1 may be prioritized according to data bandwidth or data pricing, and these information may be provided by the personal communication device 13.

The network connection handling element 43 serves several purposes—it monitors status of the hearing aid's connectivity, handles session security, and notifies the current connection information to a hearing aid location register 19a. The network connection handling element 43 may be downloaded to the personal communication device 13 from an app store and stored in a memory of the personal communication device 13.

When a hearing care professional or a monitoring server needs to exchange or collect data from the hearing aid 1, the specific hearing aid user's user account may be accessed in the user account server 25 from where the unique identity for the at least one hearing aid 1 in question may be retrieved. Preferably, the program handling the data exchange and retrieving the unique identity for the hearing aid 1 automatically sends the connection information request 31 to the control server 19, and sets up the direct connection 33, preferably using UDP hole punching, to the network connection handling element 43 based on the connection information response 32 from the hearing aid connection register 19a. The direct connection 33 is handled as described with reference to FIG. 3.

Figure 6:
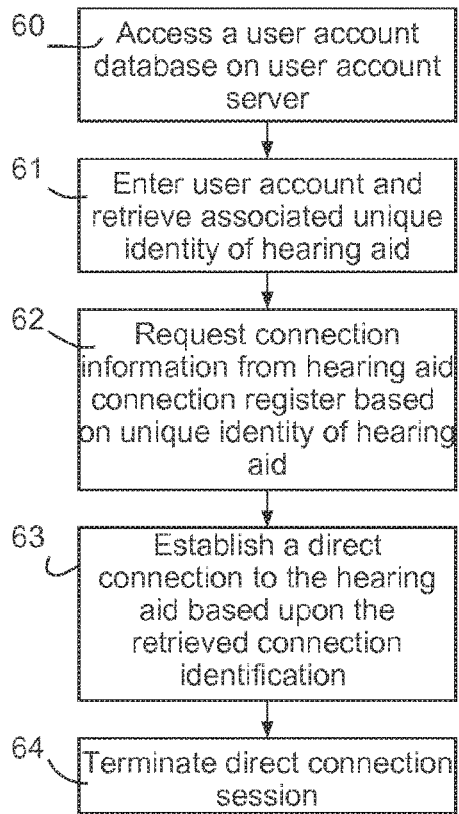
FIG. 6 illustrates a flowchart for accessing a hearing aid over the Internet according to an embodiment of the invention.

FIG. 6 illustrates a flowchart of a method for accessing a hearing aid 1 over the Internet 16 according to an embodiment of the invention. An entity, e.g. a computer (M2M—"machine-to-machine"—data consolidation) or a hearing care professional via a computer 21, intending to connect to the hearing aid 1, accesses in step 60 the user account database 26. If the entity is permitted to connect to the hearing aid 1, the entity is in step 61 able to retrieve the unique identity of the hearing aid 1 from the user account. In step 62, the entity sends the connection information request 31 containing the unique identity of the hearing aid 1 to the hearing aid connection register 19a, and receives the current connection information of the hearing aid 1 in response. In step 63, the entity sets up the direct connection 33 from a computer 21, preferably using UDP hole punching, to the network connection handling element 43 in the hearing aid 1 or in the personal communication device 13 connected to the hearing aid 1. In step 64, the entity terminates the direct connection when the exchange of data has been completed successfully.

Figure 7:
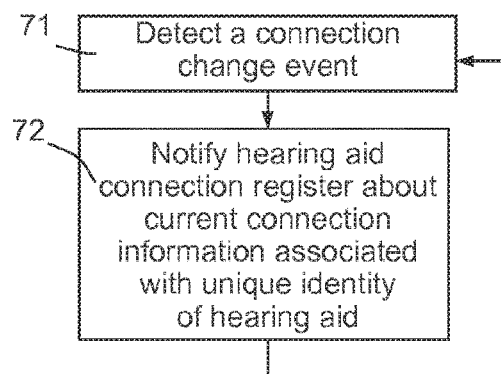
FIG. 7 illustrates a flowchart for maintaining the access data for a hearing aid according to an embodiment of the invention.

FIG. 7 illustrates a flowchart of a method for maintaining the access data for a hearing aid 1 according to an embodiment of the invention. In step 71, the network connection handling element 43 detects the presence of a connection to the Internet 16 from the hearing aid 1, or detects the presence of a connection to the Internet 16 from the personal communication terminal 13 and a short range connection to the hearing aid 1.

When sending the connection information notification 30 in step 72, the current connection information of the network connection handling element 43 is present as source address of the data packet and the unique identity for the hearing aid 1 is contained in the data packet. The control server 19 extracts these two elements and updates a hearing aid connection register 19a accordingly.

These steps are repeated every time the network connection handling element 43 detects a change in the connection information for the hearing aid 1.

Figure 8:
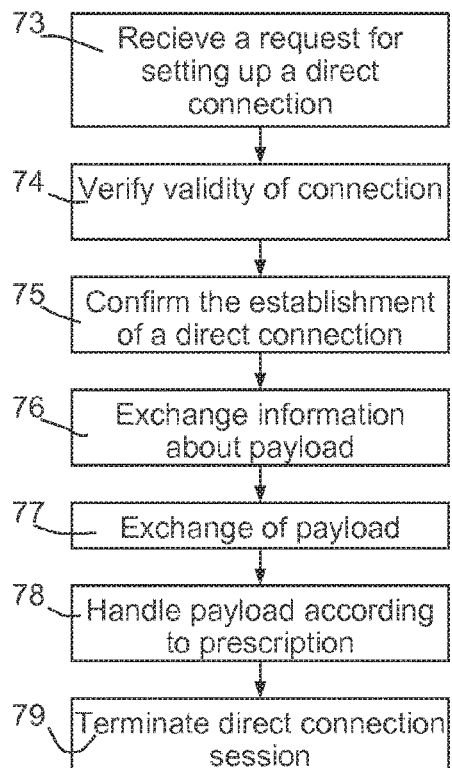
FIG. 8 illustrates a flowchart of a method for handling the establishment of a direct connection to a hearing aid according to an embodiment of the invention.

FIG. 8 illustrates a flowchart of a method for handling the establishment of the direct connection to the hearing aid 1 according to an embodiment of the invention. When the network connection handling element 43 in step 73 receives a request for setting up a direct connection 33a, it starts verifying the validity of the connection in step 74. This may include verification of certificates. If the validity of the connection has been verified, the network connection handling element 43 confirms the establishment of the direct connection 33 in step 75.

In step 76, the computer 21 communicates to the network connection handling element 43 which kind of data has to be exchanged—upload of logging data, download of settings etc. In step 77, the data requested are exchanged, and in step 78, data are handled as prescribed. New settings may overwrite earlier settings in the hearing aid 1, and logging registers may be reset if their content has been uploaded. When the data have been exchanged and handled successfully, the direct connection session is terminated in step 79.

The invention claimed is:

1. A system for managing a remote hearing care session facilitated by a hearing professional and including remote access to at least one hearing aid of a hearing aid user, and comprising:
    a hearing aid connection register provided on an internet-based server, the hearing aid connection register includes for each hearing aid a unique identity and a current connection information, wherein the hearing aid connection register is adapted for:
        updating the connection information when receiving communicated connection information from a hearing aid, and
        providing the current connection information to a computer device upon request;
    wherein the at least one hearing aid contains a network connection handling element adapted for:
        detecting the presence of a wireless connection via a gateway to the internet, and
        uploading current connection information to the hearing aid connection register when the wireless connection has been detected; and
    a computer device operated by the hearing professional and being adapted for:
        setting up the remote care session by requesting the hearing aid connection register to provide the current connection information for the at least one hearing aid, and
        establishing a connection to the at least one hearing aid based on the current connection information; and
        providing remote access to and adjustment of at least one hearing aid in the remote hearing care session facilitated by the hearing professional;
    wherein the network connection handling element is stored as software code in a hearing aid memory and run as a program by a hearing aid processor.

2. The system according to claim 1, wherein the computer device is adapted for setting up a direct connection using UDP (User Datagram Protocol) hole punching for establishing a bidirectional UDP connection.

3. The system according to claim 1, and further comprising a user account database provided on an internet-based server, the user account database includes for each hearing aid user an indication of at least one hearing aid by means a unique identity for the at least one hearing aid.

4. The system according to claim 1, wherein the network connection handling element is adapted for handling security of the remote hearing care session.

5. The system according to claim 1, wherein the connection information of the hearing aid connection register is pre-programmed into the network connection handling element.

6. The system according to claim 1, wherein the network connection handling element is adapted for transmitting the current connection information to the hearing aid connection register when trigged by an event, including one of following:

establishing a connection via a gateway to the Internet, or reconnecting to a smartphone via Bluetooth.

7. The system according to claim 1, wherein the computer device is adapted for adjusting the settings for alleviating the hearing loss in the at least one hearing aid.

8. The system according to claim 3, wherein the user account database and hearing aid connection register are provided in two separate servers.

9. The system according to claim 3, wherein the user account server is adapted for automatically updating the hearing aid connection register upon creation of new user accounts.

10. The system according to claim 1, wherein the hearing aid connection register is adapted mapping the unique identity to an IP address and port number.

11. A method of managing a remote hearing care session facilitated by a hearing professional and including remote access to at least one hearing aid of a hearing aid user, wherein the at least one hearing aid contains a network connection handling element, and wherein a computer device is operated by the hearing professional, the method comprising:
providing a hearing aid connection register on an internet-based server, the hearing aid connection register includes for each hearing aid a unique identity and a current connection information,
updating the current connection information when receiving current connection information from a hearing aid,
providing the current connection information to a computer device upon request detecting, by means of the network connection handling element, the presence of a wireless connection from the at least one hearing aid via a gateway to the internet,
uploading current connection information from the at least one hearing aid to the hearing aid connection register when the wireless connection has been detected,
setting up the remote care session from the computer device by requesting the hearing aid connection register to provide the current connection information for the at least one hearing aid,
establishing a connection from the computer device to the at least one hearing aid based on the current connection information; and
providing remote access to and adjustment of at least one hearing aid in the remote hearing care session facilitated by the hearing professional;
wherein the network connection handling element is stored as software code in a hearing aid memory and run as a program by a hearing aid processor.

12. The method according to claim 11, wherein the setting up the remote care session includes setting up a direct connection using UDP (User Datagram Protocol) hole punching for establishing a bidirectional UDP connection.

13. The method according to claim 11, and further comprising a step of providing a user account database on an internet-based server, wherein the user account database includes for each hearing aid user an indication of at least one hearing aid by means a unique identity for the at least one hearing aid.

14. The method according to claim 11, and further comprising handling security of the remote hearing care session by means of the network connection handling element.

15. The method according to claim 14, and further comprising steps of:
transmitting the current connection information from the network connection handling element to the hearing aid connection register when trigged by an event, including one of following:
establishing a connection via a gateway to the Internet, or
reconnecting to a smartphone via Bluetooth.

16. The method according to claim 11, and further comprising a step of alleviating the hearing loss in the at least one hearing aid in remote hearing care session facilitated by the hearing professional.

17. The method according to claim 11, and further comprising maintaining the user account database and hearing aid connection register in two separate servers.

18. The method according to claim 17, and further comprising automatically updating the hearing aid connection register upon creation of new user accounts in the user account database.

19. The method according to claim 11, and further comprising mapping the unique identity to an IP address and port number in the hearing aid connection register.

20. A system for managing a remote hearing care session facilitated by a hearing professional and including remote access to at least one hearing aid of a hearing aid user, and comprising:
a hearing aid connection register provided on an internet-based server, the hearing aid connection register includes for each hearing aid a unique identity and a current connection information, wherein the hearing aid connection register is adapted for:
updating the connection information when receiving communicated connection information from a hearing aid, and
providing the current connection information to a computer device upon request;
wherein the at least one hearing aid contains a network connection handling element adapted for:
detecting the presence of a wireless connection via a gateway to the internet, and
uploading current connection information to the hearing aid connection register when the wireless connection has been detected; and
a computer device operated by the hearing professional and being adapted for:
setting up the remote care session by requesting the hearing aid connection register to provide the current connection information for the at least one hearing aid, and
establishing a connection to the at least one hearing aid based on the current connection information; and
providing remote access to and adjustment of at least one hearing aid in the remote hearing care session facilitated by the hearing professional;
wherein the network connection handling element is adapted for transmitting the current connection information to the hearing aid connection register when trigged by an event, including one of following:
establishing a connection via a gateway to the Internet, or
reconnecting to a smartphone via Bluetooth.

* * * * *